United States Patent [19]

Nyilas et al.

[11] Patent Number: 4,481,353

[45] Date of Patent: Nov. 6, 1984

[54] BIORESORBABLE POLYESTERS AND POLYESTER COMPOSITES

[75] Inventors: Emery Nyilas, Austin, Tex.; Tin-Ho Chiu, Reading, Mass.

[73] Assignee: The Children's Medical Center Corporation, Boston, Mass.

[21] Appl. No.: 539,978

[22] Filed: Oct. 7, 1983

[51] Int. Cl.$^3$ .............................................. C08G 63/52
[52] U.S. Cl. .................................... 528/303; 528/272; 528/302; 528/304; 528/306
[58] Field of Search ............... 528/272, 302, 303, 304, 528/306

[56] References Cited

U.S. PATENT DOCUMENTS

| | | | |
|---|---|---|---|
| 1,091,732 | 3/1914 | Callahan | 528/272 |
| 2,195,392 | 3/1940 | Ellis | 260/75 |
| 3,068,206 | 11/1958 | Nicholson et al. | 269/75 |
| 3,296,211 | 1/1967 | Winkler | 260/75 |
| 3,346,326 | 10/1967 | Yoshifumi | 8/127.5 |
| 3,463,158 | 8/1969 | Schmitt et al. | 128/334 |
| 3,636,956 | 1/1972 | Schneider | 128/335.5 |
| 3,797,499 | 3/1974 | Schneider | 128/334 |
| 3,867,190 | 2/1975 | Schmitt et al. | 117/138 |
| 3,883,901 | 5/1975 | Coquard et al. | 3/1 |
| 3,959,200 | 5/1976 | Scott | 260/29.1 |
| 3,978,203 | 8/1976 | Wise | 528/303 X |
| 3,997,512 | 12/1976 | Casey et al. | 528/303 X |
| 4,032,993 | 7/1977 | Coquard et al. | 3/1 |
| 4,042,978 | 8/1977 | Jones et al. | 3/1 |
| 4,095,600 | 6/1978 | Casey et al. | 128/335 |
| 4,128,535 | 12/1978 | Baker | 528/272 |
| 4,140,678 | 2/1979 | Shalaby et al. | 260/860 |
| 4,201,216 | 5/1980 | Mattei | 128/335.5 |

Primary Examiner—Lucille M. Phynes

[57] ABSTRACT

Bioresorbable polyesters composed of, in one aspect, the Krebs Cycle dicarboxylic acid or isomer or anhydride thereof, chosen for the group consisting of succinic acid, fumaric acid, oxaloacetic acid, L-malic acid, and D-malic acid, a diol having 2, 4, 6, or 8 carbon atoms, and an alpha-hydroxy carboxylic acid chosen from the group consisting of glycolic acid L-lactic acid and D-lactic acid.

22 Claims, No Drawings

BIORESORBABLE POLYESTERS AND POLYESTER COMPOSITES

This invention relates to bioresorbable polyesters having medical applications.

Various types of polyesters have been used for a wide variety of purposes, including the manufacture of medical products.

The present invention provides novel polyesters which are useful in making surgical articles including sutures, ligatures and microtubular channels for aiding the regeneration and guidance of severed mammalian nerves. The new polyesters are non-toxic, non-antigenic, biodegradable, and bioresorbable; i.e. their degradation products are eliminated from the mammalian body via existing metabolic pathways. Bioresorbability is important in medical applications, and particularly in nerve guidance channels, because newly regenerated nerves are likely to be extremely sensitive to polyester decomposition products left behind by the polyester channel, which must decompose after it has fulfilled its function of promoting regeneration. The composition of the new polyesters is such that their properties can be varied within wide ranges so that they can be adapted for a wide range of medically-related purposes. The compositions of the polyesters can be controlled, for example, to provide polyesters having a variety of bulk physical properties, tackiness, brittleness, and rate of in vivo resorption.

The polyesters of the invention are all made up of the following starting materials: the Krebs Cycle ("KC") dicarboxylic acids succinic acid, fumaric acid, oxaloacetic acid, L-malic acid, the non-naturally occurring isomer D-malic acid, and the acid anhydrides of the above (all of these are hereinafter referred to as Krebs Cycle dicarboxylic acids, or "KC acids"); the alpha-hydroxy carboxylic acids indigenous to the human body, i.e. glycolic acid, L-lactic acid, the non-naturally occurring isomer D-lactic acid, and racemic lactic acid (all of these are hereinafter referred to as "alpha-hydroxy carboxylic acids"); all aliphatic diols having 2, 4, 6, or 8 carbon atoms (the diols are hereinafter referred to as "diols").

In general, the invention features, in one aspect, a bioresorbable polyester in which monomeric subunits are arranged randomly in the polyester molecules (i.e., a "random" polyester), the polyester being the condensation reaction product of a KC acid, an alpha-hydroxy carboxylic acid, and a diol. In preferred embodiments the KC acid is succinic acid, the alpha-hydroxy carboxylic acid is L-lactic acid, and the diol is 2,3-butanediol; and the polyester is made by reacting together the KC acid and the diol to form a diol monoester of the KC acid, purifying the diol monoester, and then reacting it with the alpha-hydroxy carboxylic acid.

In another aspect the invention features a bioresorbable polyester in which monomeric units are arranged nonrandomly in the polyester molecules (i.e., a "nonrandom" polyester), the polyester being made by first esterifying an alpha-hydroxy carboxylic acid or anhydride thereof with a diol (the acid:diol mole ratio is preferably 2:1) to form a hydroxyl group-terminated diester, and then purifying the diester and reacting it with a KC acid to form the nonrandom copolyester. The copolyester can be hydroxy or carboxy terminated. In a preferred embodiment the diol is 2,3 butanediol, the alpha-hydroxy carboxylic acid is L-lactic acid, and the KC acid is succinic acid.

Other features and advantages of the invention will be apparent from the following description of the preferred embodiments thereof, and from the claims.

DESCRIPTION OF THE PREFERRED EMBODIMENTS

Structure and Manufacture

The structural formulae of the starting materials named in the following description will first be given.

| Krebs Cycle Dicarboxylic Acids and Isomers Thereof | |
|---|---|
| Succinic acid | 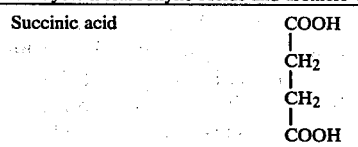 |
| Fumaric acid | 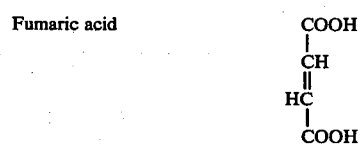 |
| Oxaloacetic acid | 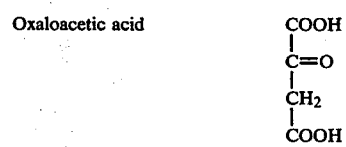 |
| L-Malic acid |  |
| D-Malic Acid | 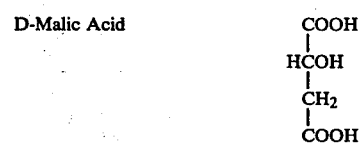 |

| Alpha Hydroxy Carboxylic Acids Indigenous to the Human Body, or Isomers Thereof | |
|---|---|
| Glycolic acid |  |
| L-Lactic acid |  |
| D-Lactic acid |  |

| Aliphatic Diols Having 2, 4, 6, or 8 Carbon Atoms | |
|---|---|
| 2,3-Butanediol | 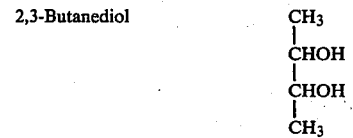 |

| | |
|---|---|
| 1,4-Butanediol | HOCH$_2$<br>\|<br>CH$_2$<br>\|<br>CH$_2$<br>\|<br>HOCH$_2$ |

The specific KC acids and alpha-hydroxy carboxylic acids listed above are the only acids encompassed by the present invention. Many diols other than 2,3-butanediol, however, are included, 2,3-butanediol just being, because it is known to be metabolizable in the mammalian body by oxidative scission, the most preferred specific example. Other diols having two to eight carbon atoms, e.g. 1,4-butanediol and 2,3-butanediol, are either commercially available or can be routinely synthesized by a chemist of ordinary skill. All of the KC and alpha-hydroxy carboxylic acids are commercially available.

In the following discussion, diols and acids will be represented generally as follows:

| | |
|---|---|
| First Diol D$_1$ or | HO—R$_{D1}$—OH, where R$_{D1}$ is an alkyl group having 2, 4, 6, or 8 carbon atoms. |
| Second Diol D$_2$ or | HO—R$_{D2}$—OH, where R$_{D2}$ is an alkyl group having 2, 4, 6, or 8 carbon atoms and is different from R$_{D1}$. |
| First KC acid A$_1$ or | HOOC—R$_{A1}$—COOH, where R$_{A1}$ is the 2-carbon group separating the two carboxyl groups |
| Second KC acid A$_2$ or | HOOC—R$_{A2}$—COOH, where R$_{A2}$ is the 2-carbon group separating the two carboxyl groups and is different from R$_{A1}$. |
| First hydroxy carboxylic acid H$_1$ or | HOOC—R$_{H1}$—OH, where R$_{H1}$ is CH$_2$ or CHCH$_3$ |
| Second hydroxy carboxylic acid H$_2$ or | HOOC—R$_{H2}$—OH, where R$_{H2}$ is CH$_2$ or CHCH$_3$ and is different from R$_{H1}$ |

For the sake of convenience and clarity, the longer chemical symbols frequently will not be used herein in representing condensation polymerization reactions, as those reactions take place according to well known principles, i.e. the way in which the reactive groups of acids and diols combine to form polyesters are well known and are described in numerous texts and patents. For example, the combination of a diol and a KC acid is a condensation reaction which can be represented as follows:

$$\text{HO—R}_D\text{—OH} + \text{HOOC—R}_A\text{—COOH} \rightarrow \text{—HO—R}_D\text{OOC—R}_A]_n \qquad (1)$$

Reaction (1) can, however, be more conveniently represented simply as $$D + A_1 \rightarrow \text{—DA}_1]_n \qquad (2)$$

(n is the degree of polymerization).

All of the reactions described herein are carried out in the complete absence of added catalysts, e.g. acid catalysts such as p-toluene sulfonic acid or camphene sulfonic acid, which are frequently used in polyester condensation reactions. This is because of our findings that it is extremely difficult, as well as impractical, to achieve a quantitative removal of catalysts from the final polyester reaction product, and that the presence of even trace amounts of catalyst in the final product render the product toxic to cultured fetal mouse spinal cord and neonatal mouse cerebellar cells.

Random Copolyesters

Random copolyesters, i.e. those in which components are arranged in the polyester molecule in a random, rather than a predetermined, order, are made by reacting together a first KC acid, a second acid which is different from the first acid and which can be a different KC acid, or an alpha-hydroxy carboxylic acid indigenous to the human body; and a diol having 2, 4, 6, or 8 carbon atoms.

When both acids are KC acids, the reaction can be illustrated by representing the components as follows:

$$(y)D + (x)A_1 + (y-x)A_2 \rightarrow \text{—DA}_1A_1DA_2DA_2A_1\text{—}$$
$$DA_1D] + H_2O \qquad (3)$$

with x and y representing numbers of moles. The polymer product can have the random structure shown in equation (3), or any other random structure.

The ratio of subunits in the copolymer product is determined by the relative values of y and x. If a 1A$_1$:1A$_2$ ratio is desired, for example, x=y−x=y/2. The arrangement of subunits is also influenced by the reactivity of the diol used with each of the two dicarboxylic acids.

Random copolyesters can be made from a diol, a KC acid, and an alpha-hydroxy carboxylic acid by combining all three components at once. However, this is generally an undesirable method because an uncontrollable mixture of homo- and copolyesters is formed in such a mixture, in parallel with the formation of the desired random copolyester. Therefore, the random copolyester is much more preferably prepared by first preparing a diol monoester of the KC acid, purifying the monoester, and then reacting the purified monoester with the alpha-hydroxy carboxylic acid, as follows:

$$D + A \rightarrow DA \qquad (4)$$

$$DA + H \rightarrow [DAHHHDA] \qquad (5)$$

The copolymer product of reaction (5) has any random sequence of subunits. The mole ratio of DA:H subunits in the copolymer product depends on the mole ratio of DA:H starting materials.

There are two additional homopolymerization reactions which occur in parallel with the reaction of equation (5). One is the condensation of DA with itself:

$$DA + DA \rightarrow \text{—DADA}] \qquad (6)$$

The other is the condensation of H with itself:

$$H + H \rightarrow -HH] \quad (7)$$

The nature of the random copolymer product is related to the rate constant of the two parallel homopolymerization reactions. When the polymerization reaction is complete, the copolymer product is separated from the homopolymerization products in the reaction mixture.

Reaction (5) can be carried out using equimolar or unequimolar amounts of monoester and diol. By varying the mole ratio, the alpha-hydroxy carboxylic acid content of the random copolyester can be controlled. The mole ratio also affects the degree of randomness of the copolyester product; when the mole ratio is not 1:1, the degree of randomness of the final product is less than when equimolar amounts are used. This is because, during the polymerization reaction, a reactant present in a small amount can be depleted before the other reactant, after which time the reactant still present undergoes essentially homopolymerization until the reaction is stopped.

As an example, a random copolymer can be made using 2,3-butanediol (B), succinic acid anhydride (S), and glycolic acid (G). First the diol monoester is formed.

$$B + S \rightarrow BS \quad (8)$$

This raction can also be represented as

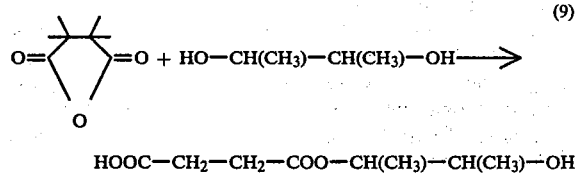

$$(9)$$

HOOC—CH$_2$—CH$_2$—COO—CH(CH$_3$)—CH(CH$_3$)—OH

A molar excess (i.e., more than a stoichiometric amount) of the monoester is then reacted with glycolic acid:

$$BS + G \rightarrow -GGBSGBSG] \quad (10)$$

This reaction can also be written as

3HOOC—CH$_2$—CH$_2$—COO—CH(CH$_3$)—CH(CH$_3$)—OH + HOOC—CH$_2$—OH → (n−1)H$_2$O +
—HOOC—CH$_2$—CH$_2$—COO—CH(CH$_3$)—CH(CH$_3$)—O]$_3$—OC—CH$_2$—O—]$_n$ (11)

The product shown above has an arbitrary random structure; the copolymer product has any random sequence of BS and L subunits.

Random copolyesters containing a diol, a KC acid, and an alpha-hydroxy carboxylic acid can be made by the following general method. A molar excess of the anhydride of the KC acid is combined with the diol and the mixture is heated to a temperature of 75° C. to 110° C. for 1½ to 5 hours, cooled, and mixed with a base to raise the pH of the mixture to 10-13. The mixture is then extracted with an organic solvent and the pH of the extract lowered to 5-7. The aqueous phase is then extracted and the organic solvent removed to leave the purified monoester.

A molar excess of the monoester is then combined with the alpha-hydroxy carboxylic acid or its anhydride, which is added slowly, over several hours, to the monoester. Vacuum melt polymerization is then carried out at a temperature of 140° to 200° C. for 2-8 hours while pressure is gradually reduced. After the pressure has been lowered to the range 0.01 to 1.5 Torr, heating to 150°-200° C. is continued for 24-48 hours.

In more detail, random (2,3-butanediol-3:1-succinate/glycolate) copolyester is made as follows.

A mixture of 50.0 g (0.50M) of succinic anhydride and 49.5 g (0.55M, 10% molar excess) of anhydrous 2,3-butanediol is heated, with rapid stirring, in the temperature range of 80° to 100° C. for 2 to 3 hours. After allowing it to cool to ambient, the straw-yellow oil obtained is stirred into 300 ml of an aqueous saturated sodium carbonate solution and, with additional amounts of sodium carbonate, the pH of the mixture is brought into the range of 11 to 12. Following an extraction of the mixture with two 50 ml portions of an organic solvent, such as ethyl ether or ethyl acetate, the pH of the aqueous phase is decreased to the range of 5.5 to 6.5 by the addition of dilute hydrochloric acid. The aqueous phase is then exhaustively extracted with either ethyl ether or ethyl acetate, followed by the removal of the organic solvent and other volatiles from the combined extracts first under atmospheric pressure and subsequently under vacuum. In order to increase its purity, the straw-yellow viscous oily residue obtained can be optionally redissolved in aqueous sodium carbonate, extracted with an organic solvent, reacidified, reextracted, and recovered from the combined extracts as described above. The product obtained with a yield of 50% or 60% of theoretical is succinic acid 2,3 butanediol monoester, HOOC—CH$_2$—CH$_2$—COO—CH(CH$_3$)—CH(CH$_3$)—OH, as verified by IR spectroscopy, molecular weight determination, and neutralization equivalent measured by titration.

To 57.0 g (0.3M) of succinic acid 2,3-butanediol monoester which are heated at 150° to 170° C. in a polymerization vessel a total of 7.6 g (0.1M) of anhydrous glycolic acid or 5.8 g (0.05M) of glycolic anhydride are added in small increments over a period of 2 to 3 hours. This is followed by subjecting the reaction mixture to vacuum melt polymerization in a manner similar to that described below for the production of copoly (2,3-butanediol-(1:1) succinate/fumarate). The crude copolyester obtained is purified twice by dissolution in tetrahydrofuran (THF) using either water or methanol as the precepitating solvent. A small amount, i.e., on the order of 0.4 to 0.6 g of the crude copolyester, is soluble only in hexafluoroisopropanol. This indicates that this by-product is either copolymer with a glycolate content which renders it insoluble in THF, or it is polyglycolic acid that is known to be soluble only in hexafluoroisopropanol.

All of the classes of random copolyesters discussed above can be either predominantly carboxy terminated or hydroxy terminated. Predominance of carboxy terminated molecules is achieved by employing, in the synthesis of copolymers, a molar excess of dicarboxylic acid, while predominance of hydroxy terminated molecules is achieved by employing a molar excess of diol.

Nonrandom Copolyesters

One class of nonrandom copolyesters, i.e. copolyesters in which components are arranged in the polyester molecule in a predetermined, monotonous order, are made from a diol, a KC acid, and an alpha-hydroxy carboxylic acid. The first step is to esterify the alpha-hydroxy carboxylic acid or its anhydride with a diol to form a diester, as follows:

$$2H + D \rightarrow HDH + H_2O \tag{12}$$

The diester product, which is essentially a diol in terms of its functionality, is then purified (there is some poly H formed) and then reacted with the KC acid or, preferably, its anhydride, as follows:

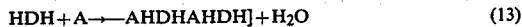
$$HDH + A \rightarrow AHDHAHDH] + H_2O \tag{13}$$

The nonrandom copolyester product can be hydroxy or carboxy terminated, depending on whether a molar excess of HDH or A is used.

Equation (12) can also be written:

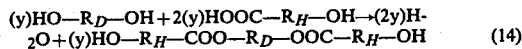
$$(y)HO-R_D-OH + 2(y)HOOC-R_H-OH \rightarrow (2y)H_2O + (y)HO-R_H-COO-R_D-OOC-R_H-OH \tag{14}$$

Equation (13) can then be expressed

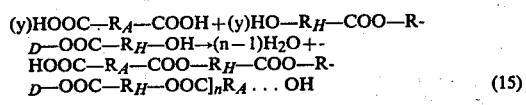
$$(y)HOOC-R_A-COOH + (y)HO-R_H-COO-R_D-OOC-R_H-OH \rightarrow (n-1)H_2O + HOOC-R_A-COO-R_H-COO-R_D-OOC-R_H-OOC]_nR_A\ldots OH \tag{15}$$

The nonrandom copolyester product of equation (15) has recurring units of $-R_A-COO-R_H-COO-R_D-OOC-R_H-OOC]$ in which $R_A$ is the 2-carbon group separating the carboxyl groups of a KC acid, $R_H$ is $CH_2$ or $CHCH_3$, and $R_D$ is an alkyl group having 2, 4, 6, or 8 carbon atoms.

Nonrandom copolyesters containing a diol, a KC acid, and an alpha-hydroxy carboxylic acid can be made by the following general method. A molar excess of the anhydrous alpha-hydroxy carboxylic acid is heated with the diol and the major portion of the water theoretically formed in the esterification reaction is removed. The pH of the ester product is raised to 10–13 and the ester product is then extracted with an organic solvent to remove unreacted acid as well as monoester. The solvent is then removed, the residue is fractionated, and the fraction corresponding to diester collected. The diester is reacted with KC acid or anhydride using a vacuum melt polymerization procedure as previously described for the preparation of random copolyesters.

As an example, a nonrandom copolyester can be made using 1,4 butanediol (B), succinic acid (S), and L-lactic acid (L). First a molar excess of the L-lactic acid (or its anhydride) is esterified with the diol:

$$2L + B \rightarrow LBL + 2H_2O \tag{16}$$

This reaction can also be written:

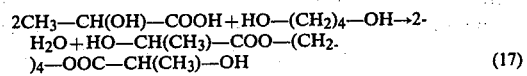
$$2CH_3-CH(OH)-COOH + HO-(CH_2)_4-OH \rightarrow 2H_2O + HO-CH(CH_3)-COO-(CH_2)_4-OOC-CH(CH_3)-OH \tag{17}$$

The diester product is isolated and purified via high vacuum distillation and then reacted with succinic acid anhydride:

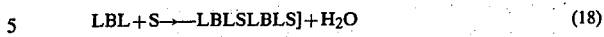
$$LBL + S \rightarrow LBLSLBLS] + H_2O \tag{18}$$

This reaction can also be written:

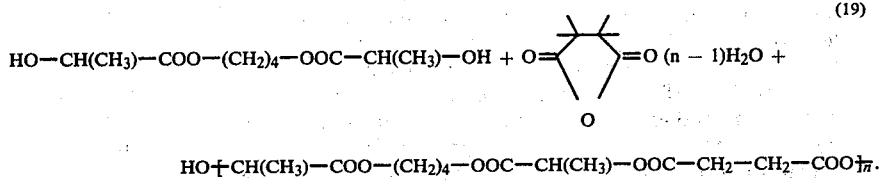

$$HO-CH(CH_3)-COO-(CH_2)_4-OOC-CH(CH_3)-OH + O{=}\!\!\left\langle\begin{array}{c}\\ \\O\end{array}\right\rangle\!\!{=}O \rightarrow (n-1)H_2O +$$

$$HO\mbox{+}CH(CH_3)-COO-(CH_2)_4-OOC-CH(CH_3)-OOC-CH_2-CH_2-COO\mbox{+}_n. \tag{19}$$

In more detail, the nonrandom copolyester product is made as follows.

In a three-necked flask which is equipped with a distilling side-arm and a thermometer each for measuring the bulk-phase and vapor phase temperatures, 297 g (3.3M, 10% molar excess) of anhydrous D, L-(+)-lactic acid are heated with 135 g (1.5M) of anhydrous 1,4-butanediol such as to maintain the vapor phase temperature in the range of 100° to 115° C. After collecting more than 95% of the amount of water that is to be theoretically formed in, and eliminated from, this esterification reaction, the syrup obtained is rapidly stirred into 400 ml of a saturated aqueous sodium carbonate solution at ambient temperature. While maintaining the aqueous suspension in the pH range of 11 to 12, it is exhaustively extracted with ethyl ether or ethyl acetate, or another suitable water-immiscible solvent leaving the sodium salts of any unreacted lactic acid, of lactic acid oligomers formed potentially, and of the lactic acid 1,4-butanediol monoester, in the aqueous phase. Following the drying of the combined extracts over anhydrous sodium sulfate, the organic extracting solvent is removed under atmospheric pressure and the residue is subjected to fractionation under high vacuum. The diester fraction is collected at 155° to 175° C. under 0.05 to 0.1 Torr pressure.

The diester is then reacted with succinic anhydride to form the nonrandom copolyester product, and the product is then purified. These steps are carried out in a manner similar to the vacuum-melt polyermization reaction and precipitative purification steps described below for the production and purification of copoly-(2,3-butanediol-1:1-succinate/fumarate).

Instead of the naturally occurring L-lactic acid, D-lactic acid or a racemic mixture of L- and D-lactic acids can be used. The form which is used affects the properties of the final copolyester product, particularly the in vivo bioresorption rate.

The differences in resorption rates between L- and D-isomers of lactic and malic acid can be exploited as a means of manipulating the resorption rate of, e.g. implantable devices such as nerve guidance channels. The proper isomers are selected so that the resorption rate of the device suits its function. Nerve guidance channels, for example, must be resorbed only after the nerve has regenerated, but must retain mechanical integrity for long enough to permit regeneration.

The ability to determine whether the nonrandom copolyester product is predominantly hydroxy or carboxy-terminated offers yet another means for controlling the properties of the product, since hydroxy and carboxy terminated isomers of the same copolyester possess distinctly different bulk physical, surface, and hence biological properties.

Another class of nonrandom copolyesters are made from a diol and two different KC acids. The first step is to react a large molar excess of diol with the first KC acid to assure the formation of a diester, as follows:

$$3D + A_1 \rightarrow DA_1D + H_2O + D \quad (20)$$

The diester $DA_1D$ is then isolated from the reaction mixture via high vacuum distillation. The diester, which is essentially a diol in terms of its functionality, can then be combined with the second KC acid in a condensation reaction:

$$DA_1D + A_2 \rightarrow -DA_1DA_2DA_1DA_2] \quad (21)$$

The product can be carboxy or hydroxy terminated.

Equation (20) can also be written:

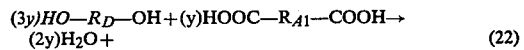
$$(3y)HO-R_D-OH + (y)HOOC-R_{A1}-COOH \rightarrow$$
$$(2y)H_2O + \quad (22)$$

$(y)HO-R_D-OOC-R_{A1}-COO-R_D-OH + (y)-HO-R_D-OH$ (excess diol).

Equation (21) can then be expressed:

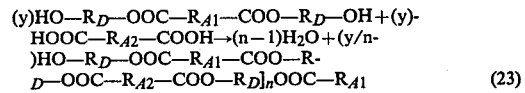
$$(y)HO-R_D-OOC-R_{A1}-COO-R_D-OH + (y)-HOOC-R_{A2}-COOH \rightarrow (n-1)H_2O + (y/n-)HO-R_D-OOC-R_{A1}-COO-R-D-OOC-R_{A2}-COO-R_D]_nOOC-R_{A1} \quad (23)$$

The nonrandom product of equation (21) has recurring units of $-OOC-R_{A1}-COO-R_D-OOC-R_{A2}-COO-R_D]$ in which $R_{A1}$ and $R_{A2}$ are different from each other and are each the 2-carbon group separating the carboxyl groups of a KC acid and $R_D$ is an alkyl group having 2, 4, 6, or 8 carbon atoms.

Reaction (19), although it can be carried out using any KC acid, proceeds with the greatest ease, and with a minimum of competing side reactions, when the dicarboxylic acid is one which is convertible to its corresponding acid anhydride. Most preferably the acid anhydride is a ring anhydride. As succinic acid is the only Krebs Cycle dicarboxylic acid which forms such a ring anhydride, succinic acid anhydride is the most preferred acid anhydride. The reaction between a diol and succinic acid anhydride to prepare a hydroxyterminated diester intermediate can be represented as follows:

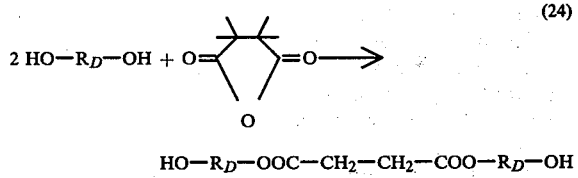
$$HO-R_D-OOC-CH_2-CH_2-COO-R_D-OH$$

When carrying out reaction (20) using a KC acid rather than an anhydride, the diester is formed by reacting the acid and diol and then stopping the reactions after one molar equivalent of water has left the diester product.

Nonrandom copolyesters containing a diol and two different KC acids can be made by the following general method. A molar excess of the diol is heated to 110°–150° C. and the anhydride of one of the KC acid is added slowly over a period of 1–2 hours. The mixture is then heated to 140° C.–200° C. for 4–10 hours and water and excess diol stripped from the product of the condensation reaction. The pH is raised to 10–13 and the product is extracted with an organic solvent, leaving unreacted KC acid and monoester in the aqueous phase. The organic solvent is then removed, the remaining product is fractionated, and the fraction corresponding to the diester collected. The diester is reacted with the second KC acid using a vacuum melt procedure as previously described for the preparation of random copolyesters.

An example of a nonrandom copolyester in the above class is copoly(2,3-butanediol-1:1-succinate/fumarate). This polyester is made according to the two-step procedure generally described above. In the first step, a molar excess of 2,3-butanediol is reacted with succinic anhydride:

$$2\ HO-CH(CH_3)-CH(CH_3)-OH + \quad (25)$$

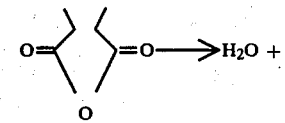
$$\rightarrow H_2O +$$

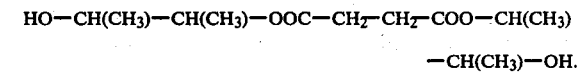
$$HO-CH(CH_3)-CH(CH_3)-OOC-CH_2-CH_2-COO-CH(CH_3)$$
$$-CH(CH_3)-OH.$$

The diester is then reacted with the second KC acid, fumaric acid, to form the nonrandom copolyester product:

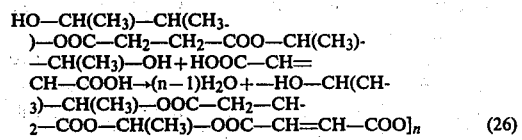
$$HO-CH(CH_3)-CH(CH_3-)-OOC-CH_2-CH_2-COO-CH(CH_3)-$$
$$-CH(CH_3)-OH + HOOC-CH=$$
$$CH-COOH \rightarrow (n-1)H_2O + -HO-CH(CH_3)-CH(CH_3)-OOC-CH_2-CH_2-COO-CH(CH_3)-OOC-CH=CH-COO]_n \quad (26)$$

In more detail, the nonrandom copolyester is made as follows. To 54.1 g (0.6 M, 50% molar excess) of anhydrous 2,3-butanediol which is maintained, in a suitable vessel, in the temperature range of 130° to 140° C. with continuous stirring, 20.1 g (0.2M) of succinic anhydride are added in small increments over a period of 60 to 90 min. After increasing the temperature to 160° to 180° C. for a period of 6 to 8 hours, the mixture is stripped under increasing vacuum of the water formed in the condensation reaction and most of the excessive diol. The viscous residue obtained is dispersed, with rapid stirring at ambient temperature, into 250 ml of saturated aqueous sodium carbonate and, if necessary, small amounts of sodium carbonate are added to maintain the pH of the suspension in the pH range of 11 to 12. The alkaline aqueous suspension is extracted three or four times with ethyl ether or ethyl acetate, leaving the sodium salts of any unreacted succinic acid and the succinic acid 2,3-butanediol monoester, $HOOC-CH_2-CH_2-COO-CH(CH_3)-CH(CH_3)-OH$ in the aqueous phase. Following the drying of the combined extracts over anhydrous sodium sulfate, the organic solvent is removed under atmospheric pressure leaving a syrupy residue which is subjected to fractionation under high vacuum. The fraction collected at 240° to 260° C. at 0.05 to 0.1 Torr is the 2,3-butanediol diester of succinic acid, $HO-CH(CH_3)-CH(CH_3)-OOC-CH_2-CH_2-COO-CH(CH_3)-CH(CH_3)-OH$ obtained with overall yields in the range of 40% to 75%, depending on the efficacy of the vacuum fractionation. Molecular weight determination and the IR spectrum of the fraction obtained as above confirm the structure of the 2,3-butanediol ester of succinic acid.

In a suitable polymerization tube which is equipped with a side arm and a thermometer each for measuring the bulk-phase and the vapor-phase temperatures, 28.8 g (0.11 M, 10% molar excess) of succinic acid 2,3-butanediol ester are heated, at 150° to 180° C., with 7.0 g (0.06 M) of fumaric acid until this amount of the acid has reacted, as observed from the formation of vapors of water which is eliminated in the condensation reaction. After the introduction of an additional amount of 4.6 g (0.04 M) of fumaric acid into the polymerization mixture, heating at 160° to 180° C. is continued for 3 to 6 hours while the mixture is subjected to increasing vacuum. Under reduced pressures in the range of 0.01 to 1.0 Torr, heating in the range of 160° to 200° C. is continued for 24 to 48 hours. The material obtained is purified twice by reprecipitation from an appropriate solvent such as acetone or tetrahydrofuran (THF) giving the nonrandom copolymer with a yield in the range of 60% to 85%, depending on the conditions used in the reprecipitative purification. As determined by gel permeation (or high pressure liquid) chromatography in absolute THF, the average molecular weights of copolymers obtained with this method is in the range of 15,000 to 22,000 Daltons.

An $^1$H NMR spectrum of the nonrandom copolymer confirmed the 1:1 ratio of succinic acid and fumaric acid moieties as well as indicated that at least 99.5% of the double bonds introduced via the fumaric acid moieties had a trans conformation, confirming the stereospecificity of the copolymer.

Another class of nonrandom copolyesters are made from a KC acid and two different diols. The first step is to react the first diol with a molar excess of the KC acid to form a diester, as follows:

$$2A + D_1 \rightarrow AD_1A \tag{27}$$

Preferably the acid anhydride is used, most preferably succinic acid anhydride.

The reaction between a diol and a molar excess of succinic acid anhydride to form a carboxy-terminated diester can be representd as follows:

(28)

$HOOC-CH_2-CH_2-COO-R_D-OOC-CH_2-CH_2-COOH$

When carrying out reaction (28) using a KC acid rather than an anhydride, the diester is formed by reacting the acid and diol and then the reaction is stopped after one molar equivalent of water has left the diester product.

In terms of its functionality, the diester product of reaction (27) is essentially a dicarboxylic acid capable of undergoing condensation with the second diol. The diester produced in reaction (27) is separated from the reaction mixture on the basis of solubility and is then reacted with the second diol:

$$AD_1A + D_2 \rightarrow -AD_1AD_2AD_1AD_2- \tag{29}$$

Equation (29) can also be written:

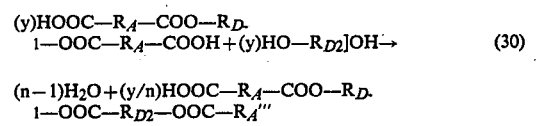

The nonrandom product of equation 30 has recurring units of $[R_A-COO-R_{D1}-OOC-R_{D2}]$ in which $R_A$ is the 2-carbon group separating the carboxyl groups of a KC acid and $R_{D1}$ and $R_{D2}$ are different from each other and are each an alkyl group having 2, 4, 6, or 8 carbon atoms.

The copolymer molecules can, at both ends, be either hydroxy or carboxy terminated; the ratio of hydroxy to carboxy terminated ends is 1:1 when the starting materials are present in a mole ratio of 1:1, as shown in equation (30). A predominance of one or the other terminating groups can be achieved by employing, in the synthesis of copolymer, a slight molar excess of the appropriate starting material.

Fumaric Acid Polyesters

Polyesters can be made by reacting a diol with fumaric acid, according to the equation

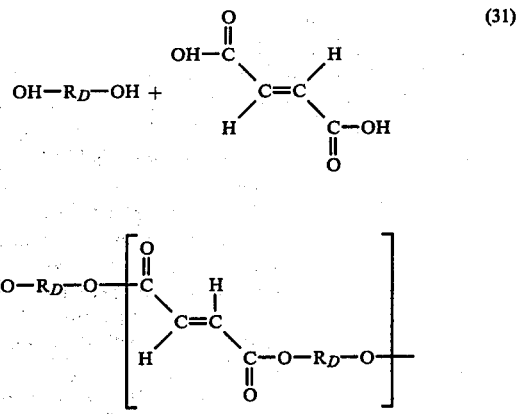

The polyester product can contain molecules which at both ends are predominantly hydroxy or carboxy terminated; the desired ratio is achieved by using a molar excess of diol or fumaric acid.

Fumaric acid is an unsaturated dicarboxylic acid in the trans-conformation. This structure can, when combined with a diol, undergo side reactions involving the double bond, in addition to the condensation reaction. These side reactions are probably free radical-induced addition polymerizations and are, we have found, easily detectable by a reddish-orange discoloration in the reactive mixture.

The product of equation (31) was, in one experiment, produced under conditions which caused a reddish-orange discoloration in the final purified product. The NMR spectrum of this product showed the presence of double bonds other than the trans double bond of the fumaric acid subunit. In cell culture evaluation, this material was found to be cytotoxic.

In contrast, the polyester product of equation (31) was, in a second experiment, produced under conditions which caused no discoloration. This product was found to contain only double bonds attributable to the trans double bond of fumaric acid, and was found to be conducive, in cell culture, to the growth of axons and the attachment of neutrons.

Composite Polyesters

Composite polyesters are formed by mixing together in a common solvent two different polyesters and then removing the solvent to allow the composite product to solidify. The first polyester is a copolyester made according to any one of the reactions of equations (1)-(31). the second polyester is (a) a copolyester made according to one of the reactions of equations (1)-(31) and which is different from the first copolyester, or (b) a polymer of an alpha-hydroxy carboxylic acid indigenous to the human body, or a polyester produced by the reaction of a diol and (c) one or (d) two alpha-hydroxy carboxylic acids indigenous to the human body.

The copolyesters (a) have already been described. The poly acids (b) are simply the condensation products of alpha-hydroxy acid molecules with each other. The reaction is formally represented as follows:

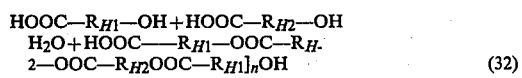

$$\text{HOOC—R}_{H1}\text{—OH} + \text{HOOC—R}_{H2}\text{—OH}$$
$$\text{H}_2\text{O} + \text{HOOC}\text{——R}_{H1}\text{—OOC—R}_{H^-}$$
$$2\text{—OOC—R}_{H2}\text{OOC—R}_{H1}]_n\text{OH} \qquad (32)$$

In reaction (32) each $R_{H1}$ and $R_{H2}$ can be $CH_2$ or $CH(CH_3)$; i.e. each acid is glycolic or lactic acid; the product may be just polylactic or polyglycolic acid; i.e. $R_{H1}$ can be the same as $R_{H2}$. The reaction product has a carboxy terminus and a hydroxy terminus.

Condensation reaction (32), although a convenient way of illustrating poly acid formation, does not represent the preferred way of obtaining a desirably high molecular weight product. Practically, high molecular weight poly acids are formed only by first converting the alpha-hydroxy acid into its anhydride and subsequently subjecting the anhydride to a ring-opening thermal polymerization reaction, as described in, e.g., U.S. Pat. No. 2,668,162, hereby incorporated by reference.

Composite provide an additional opportunity to manipulate the properties, e.g. the bulk physical properties, of the polyester product. For example, some polyesters individually have desirable biological qualities, i.e. they are conducive to cell growth, but lack useful physical characteristics. Such polyesters can be combined, in a composite, with a different polyesters which provides the desired physical properties. An example is polyglycolic acid, which by itself is unsuited for certain medical applications, despite its compatibility with cultured mammalian cells, because of its hardness and brittleness. Poly(2,3-butylene succinate) also exhibits favorable biological characteristics but, at room and body temperatures, is too tacky for most medical applications, even at high molecular weights. Three composites (3:1, 1:1, 1:3, by weight) of the two polyesters ameliorated the unfavorable physical properties of both, exhibiting varying degrees of brittleness, depending on proportions. It was also found that the composites exhibited biological degradation rates different from that of either of the polyesters alone. The above composite was made by dissolving both polyesters in a common solvent, hexafluoroisopropanol (the only solvent capable of dissolving polyglycolic acid), and then removing the solvent to allow the composite to solidify.

Nerve Guidance Channels

A number of factors must be taken into account in choosing a polyester product for use in nerve guidance channels. We have shown that the best materials, i.e. those which induce favorable degrees of neuron attachment and cell growth, are those which exhibit surface force fields in which dispersion forces are dominant, as determined from surface wettability spectra, and in which polar forces represent only a small fraction of the surface free energy. Most preferably, the ratio of polar to dispersion forces is less than 0.30. Polyester products exhibiting this low ratio give rise to force fields which induce optimal adhesive interaction with the outer surfaces of axonal growth cones. The copolyester which is currently preferred for nerve growth channels, on the basis of these criteria and in vivo tests, is random copoly (2,3-butanediol-1:1 succinate/fumarate), which was used to make nerve channels which induced nerve regeneration in mice, exhibited no toxic effects, and which is bioresorbable. The composite polyester product which is currently preferred for nerve guidance channels is 1:1 polyglycolic acid/poly(2,3-butylene succinate).

Nerve guidance channels are made by a dip-molding technique involving dipping a mandrel of desired diameter (24 $\mu$m-250 $\mu$m) into the solution of a polyester or polyester mixture, allowing the polyesters to solidify by drying, and then cooling the mandrel to shrink it so the hollow polyester channel can be removed.

Other embodiments are within the following claims.

We claim:

1. A bioresorbable polyester in which monomeric subunits are arranged randomly in the polyester molecules, said polyester comprising the condensation reaction product of
   a Krebs Cycle dicarboxylic acid or isomer or anhydride thereof, chosen for the group consisting of succinic acid, fumaric acid, oxaloacetic acid, L-malic acid, and D-malic acid,
   a diol having 2, 4, 6, or 8 carbon atoms, and
   an alpha-hydroxy carboxylic acid chosen from the group consisting of glycolic acid, L-lactic acid and D-lactic acid.

2. The polyester of claim 1 wherein, said polyester is made by
   reacting together said Krebs Cycle dicarboxylic acid and said diol to form a diol monoester of said Krebs Cycle dicarboxylic acid, purifying said diol monoester, and
   reacting said purified diol monoester with said alpha-hydroxy carboxylic acid to form said random polyester.

3. The polyester of claim 1 or claim 2 wherein said diol is 2,3-butanediol, said Krebs Cycle dicarboxylic acid is succinic acid, and said alpha-hydroxy carboxylic acid is L-lactic acid.

4. A bioresorbable polyester in which monomeric subunits are arranged randomly in the polyester molecules, said polyester comprising the condensation reaction product of
   a Krebs Cycle dicarboxylic acid or an isomers or anhydride thereof which is chosen from the group consisting of succinic acid, fumaric acid, oxaloacetic acid, L-malic acid, and D-malic acid,
   an alpha-hydroxy carboxylic acid chosen from the group consisting of glycolic acid, L-lactic acid, and D-lactic acid, racemic lactic acid, and
   a diol having 2, 4, 6, or 8 carbon atoms.

5. A nonrandom bioresorbable polyester containing recurring subunits of the formula $$-R_A-COO-R_H-COO-R_D-OOC-R_H-OOC]$$

wherein $R_A$ is the 2-carbon group separating the carboxyl groups of a dicarboxylic acid chosen from the group consisting of succinic acid, fumaric acid, oxaloacetic acid, L-malic acid, and D-malic acid, $R_H$ is $CH_2$ or $CHCH_3$, and $R_D$ is an alkyl group having 2, 4, 6, or 8 carbon atoms.

6. The bioresorbable polyester of claim 5, said polyester being made from
an alpha-hydroxy carboxylic acid, H chosen from the group consisting of glycolic acid, L-lactic acid, and D-lactic acid,
a Krebs Cycle dicarboxylic acid, A or isomer or anhydride thereof chosen from the group consisting of succinic acid, fumaric acid, oxaloacetic acid, L-malic acid, and D-malic acid, and
a diol D having 2, 4, 6, or 8 carbon atoms,
said polyester being made by the steps of
esterifying a molar excess of said alpha-hydroxy carboxylic acid or its anhydride with said diol to form a diester, according to the reaction
$H + D \rightarrow HDH + H_2O$,
purifying said diester, and
reacting said purified diester with said Krebs Cycle dicarboxylic acid or isomer or anhydride thereof to form said nonrandom polyester, according to the reaction $HDH + A \rightarrow [AHDHAHDH]$.

7. The nonrandom polyester of claim 6 wherein said diol is 2,3-butanediol, said alpha-hydroxy carboxylic acid is L-lactic acid, said Krebs Cycle dicarboxylic acid is succinic acid and said polyester is further made from D-lactic acid.

8. The nonrandom polyester of claim 6 or claim 7 wherein said polyester molecules are predominantly hydroxy terminated.

9. The nonrandom polyester of claim 6 or claim 7 wherein said polyester molecules are primarily carboxy terminated.

10. A nonrandom bioresorbable polyester containing recurring subunits of the formula $$-OOC-R_{A1}-COO-R_D-OOC-R_{A2}-COO-R_D]$$

wherein $R_{A1}$ and $R_{A2}$ are different from each other and are each the 2-carbon group separating the carboxyl groups of a dicarboxylic acid chosen from the group consisting of succinic acid, fumaric acid, oxaloacetic acid, L-malic acid, and D-malic acid, and $R_D$ is an alkyl group having 2, 4, 6, or 8 carbon atoms.

11. The bioresorbable polyester of claim 10, said polyester being made from
two Krebs Cycle dicarboxylic acids or isomers or anhydrides thereof which are different from each other and which are chosen from the group consisting of succinic acid, fumaric acid, oxaloacetic acid, L-malic acid, and D-malic acid, and
a diol having 2, 4, 6, or 8 carbon atoms,
said nonrandom polyester being made by the steps of
reacting a molar excess of said diol with one of said Krebs Cycle dicarboxylic acids or isomers or anhydrides thereof to form a diester, according to the reaction $D + A_1 \rightarrow DA_1D + H_2O$, purifying said diester, and
reacting said purified diester with said remaining Krebs Cycle dicarboxylic acid or isomers or anhydride thereof to form said nonrandom polyester, according to the reaction $DA_1D + A_2 \rightarrow [DA_1DA_2DA_1DA_2]$.

12. The nonrandom polyester of claim 10 or claim 11 wherein said polyester molecules are predominantly hydroxy terminated.

13. The nonrandom polyester of claim 10 or 11 wherein said polyester molecules are predominantly carboxy terminated.

14. A nonrandom bioresorbable polyester containing recurring subunits of the formula $$-R_A-COO-R_{D1}-OOC-R_{D2}]$$

wherein $R_A$ is the 2-carbon group separating the carboxyl groups of a dicarboxylic acid chosen from the group consisting of succinic acid, fumaric acid, oxaloacetic acid, L-malic acid, and D-malic acid, and $R_{D1}$ and $R_{D2}$ are different from each other and are each an alkyl group having 2, 4, 6, or 8 carbon atoms.

15. The bioresorbable polyester of claim 14, said polyester being made from
a Krebs Cycle dicarboxylic acid or isomer or anhydride thereof chosen from the group consisting of succinic acid, fumaric acid, oxaloacetic acid, L-malic acid, and D-malic acid, and
two diols which are different from each other and which each have 2, 4, 6, or 8 carbon atoms,
said polyester being made by the steps of
reacting one of said diols with a molar excess of said Krebs Cycle dicarboxylic acid or isomer or anhydride thereof to form a diester, according to the reaction $A + D_1 \rightarrow AD_1A$;

purifying said diester, and
reacting said purified diester with said other diol to form said nonrandom polyester, according to the reaction $AD_1A + D_2 \rightarrow [AD_1AD_2AD_1AD_2]$.

16. The nonrandom polyester of claim 15 wherein said Krebs Cycle dicarboxylic acid is reacted with said diol in the form of its acid anhydride.

17. The nonrandom polyester of claim 16 wherein said anhydride is the anhydride of succinic acid.

18. A bioresorbable polyester in which monomeric subunits are arranged nonrandomly in the polyester molecules, said polyester comprising the condensation reaction product of
fumaric acid, and
a diol having 2, 4, 6, or 8 carbon atoms.

19. The bioresorbable polyester of claim 18 having recurring subunits of the formula

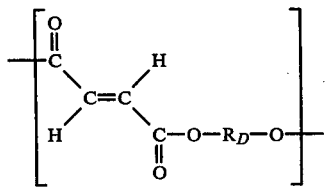

wherein $R_D$ is an alkyl group having 2, 4, 6, or 8 carbon atoms.

20. The polyester of claim 18 or claim 19 wherein said polyester molecules are predominantly hydroxy terminated.

21. The polyester of claim 18 or 19 wherein said polyester molecules are predominantly carboxy terminated.

22. A bioresorbable composite polyester comprising the product formed by mixing together in a common solvent two different polyesters and then removing the solvent to allow the product to solidify, one of said two polyesters being the polyester of any one of claims 1, 4, 5, 10, 14, or 18, and the other of said two polyesters being different from the first polyester and being one of the following:

the polyester of any one of claims 1, 4, 5, 10, 14, or 18, a polyester which is the polymeric condensation product of one or more of the alpha-hydroxy carboxylic acids glycolic acid, L-lactic acid, and D-lactic acid, or a polyester which is the polymeric condensation product of an alpha-hydroxy carboxylic acid chosen from the group consisting of glycolic acid, L-lactic acid, and D-lactic acid with one or two Krebs Cycle dicarboxylic acids or isomers or anhydrides thereof chosen from the group consisting of succinic acid, fumaric acid, oxaloacetic acid, L-malic acid, and D-malic acid.

* * * * *

UNITED STATES PATENT AND TRADEMARK OFFICE
CERTIFICATE OF CORRECTION

PATENT NO. : 4,481,353
DATED : November 6, 1984
INVENTOR(S) : Nyilas et al.

It is certified that error appears in the above-identified patent and that said Letters Patent are hereby corrected as shown below:

Col. 1, insert as the first paragraph which was omitted:

--The invention described herein was made in the course of work under a grant or award fromthe United States Government, and the Government therefore has rights in the invention.--

Col. 3, beginning on line 66,

"$HO - R_D - OH + HOOC - R_A - COOH \rightarrow HO - R_D OOC - R_A]_n$" should be -- $HO - R_D - OH + HOOC - R_A - COOH \rightarrow [HO - R_D - OOC - R_A]_n$ --.

Col. 4, beginning on line 3,

"$D + A_1 \rightarrow DA_1]_n$" should be -- $D + A_1 \rightarrow [DA_1]_n$ --.

UNITED STATES PATENT AND TRADEMARK OFFICE
CERTIFICATE OF CORRECTION

PATENT NO. : 4,481,353
DATED : November 6, 1984
INVENTOR(S) : Nyilas et al.

It is certified that error appears in the above-identified patent and that said Letters Patent are hereby corrected as shown below:

Col 4, beginning on line 31,

"$(y)D + (x)A_1 + (y-x)A_2 \longrightarrow DA_1A_1DA_2DA_2A_1DA_1D]+H_2O$" should be -- $(y)D + (x)A_1 + (y-x)A_2 \longrightarrow [DA_1A_1DA_2DA_2A_1DA_1D]+H_2O$ --.

Col. 4, line 66, "$DA + DA \longrightarrow DADA]$" should be
-- $DA + DA \longrightarrow [DADA]$ --.

Col. 5, line 1, "$H + H \longrightarrow HH]$" should be
-- $H + H \longrightarrow [HH]$ --.

Col. 5, line 41, "$BS + G \longrightarrow GGBSGBSG]$" should be
-- $BS + G \longrightarrow [GGBSGBSG]$ --.

Col. 5, beginning on line 46,

"$3HOOC-CH_2-CH_2-COO-CH(CH_3)-CH(CH_3)-OH + HOOC-CH_2-OH \longrightarrow$ $(n-1)H_2O + HOOC-CH_2-CH_2-COO-CH(CH_3)-CH(CH_3)-O]_3-OC-CH_2-$ $O-]_n$" should be

UNITED STATES PATENT AND TRADEMARK OFFICE
CERTIFICATE OF CORRECTION

PATENT NO. : 4,481,353
DATED : November 6, 1984
INVENTOR(S) : Nyilas et al.

Page 3 of 7

It is certified that error appears in the above-identified patent and that said Letters Patent are hereby corrected as shown below:

-- $3HOOC-CH_2-CH_2-COO-CH(CH_3)-CH(CH_3)-OH + HOOC-CH_2-OH \longrightarrow$ $(n-1) H_2O + [HOOC-CH_2-CH_2-COO-CH(CH_3)-CH(CH_3)-O]_3-OC-CH_2-O]_n$ --.

Col. 7, line 21, "HDH + A$\longrightarrow$AHDHAHDH] + $H_2O$" should be --HDH + A$\longrightarrow$[AHDHAHDH]. + $H_2O$ --.

Col. 7, beginning on line 31,
"$(y)HOOC-R_A-COOH + (y)HO-R_H-COO-R_D-OOC-R_H-OH \longrightarrow (n-1)H_2O + HOOC-R_A-COO-R_H-COO-R_D-OOC-R_H-OOC]_n R_A \ldots OH$" should be
-- $(y)HOOC-R_A-COOH + (y)HO-R_H-COO-R_D-OOC-R_H-OH \longrightarrow (n-1)H_2O + HOOC[R_A-COO-R_H-COO-R_D-OOC-R_H-OOC]_n R_A \ldots OH$ --.

UNITED STATES PATENT AND TRADEMARK OFFICE
CERTIFICATE OF CORRECTION

PATENT NO. : 4,481,353

DATED : November 6, 1984

INVENTOR(S) : Nyilas et al.

It is certified that error appears in the above-identified patent and that said Letters Patent are hereby corrected as shown below:

Col. 7, beginning on line 37, "—$R_A$—COO—$R_H$—COO—$R_D$—OOC—$R_H$—OOC]" should be

-- [$R_A$—COO—$R_H$—COO—$R_D$—OOC—$R_H$—OOC] --.

Col. 8, line 5, "LBL + S⟶LBLSLBLS]+$H_2$O" should be --LBL + S⟶[LBLSLBLS]+$H_2$O --.

Col. 9, line 15, "$DA_1D + A_2$⟶$DA_1DA_2DA_1DA_2$]" should be --$DA_1D + A_2$⟶[$DA_1DA_2DA_1DA_2$] --.

Col. 9, beginning on line 26, "(y)HO—$R_D$—OOC—$R_{A1}$—COO—$R_D$—OH+(y)HOOC—$R_{A2}$—COOH⟶(n-1)$H_2$O + (y/n)HO—$R_D$—OOC—$R_{A1}$—COO—$R_D$—OOC—$R_A$2—COO—$R_D$]$_n$OOC—$R_{A1}$" should be --(y)HO—$R_D$—OOC—$R_{A1}$—COO—$R_D$—OH+(y)HOOC—$R_{A2}$—COOH⟶(n-1)$H_2$O +(y/n)HO—$R_D$—[OOC—$R_{A1}$—COO—$R_D$—OOC—$R_{A2}$—COO—$R_D$]$_n$ OOC--$R_{A1}$ --.

UNITED STATES PATENT AND TRADEMARK OFFICE
CERTIFICATE OF CORRECTION

PATENT NO. : 4,481,353

DATED : November 6, 1984

INVENTOR(S) : Nyilas et al.

It is certified that error appears in the above-identified patent and that said Letters Patent are hereby corrected as shown below:

Col. 9, beginning on line 32, "$-OOC-R_{A1}-COO-R_D-OOC-R_{A2}-COO-R_D$]" should be --$[OOC-R_{A1}-COO-R_D-OOC-R_{A2}-COO-R_D]$ --.

Col. 10, beginning on line 33, "$HO-CH(CH_3)-CH(CH_3)-OOC-CH_2-CH_2-COO-CH(CH_3)-CH(CH_3)-OH + HOOC-CH = CH-COOH \longrightarrow (n-1)H_2O + -HO-CH(CH_3)-CH(CH_3)-OOC-CH_2-CH_2-COO-CH(CH_3)-OOC-CH = CH-COO]_n$" should be --$HO-CH(CH_3)-CH(CH_3)-OOC-CH_2-CH_2-COO-CH(CH_3)-CH(CH_3)-OH + HOOC-CH = CH-COOH \longrightarrow (n-1)H_2O + [HO-CH(CH_3)-CH(CH_3)-OOC-CH_2-CH_2-COO-CH(CH_3)-OOC-CH = CH-COO]_n$ --.

Col. 11, line 66, "$AD_1A + D_2 \longrightarrow AD_1AD_2AD_1AD_2-$" should be --$AD_1A + D_2 \longrightarrow [AD_1AD_2AD_1AD_2]$ --.

UNITED STATES PATENT AND TRADEMARK OFFICE
CERTIFICATE OF CORRECTION

PATENT NO. : 4,481,353

DATED : November 6, 1984

INVENTOR(S) : Nyilas et al.

It is certified that error appears in the above-identified patent and that said Letters Patent are hereby corrected as shown below:

Col. 12, beginning on line 2, "(y)HOOC—$R_A$—COO—$R_{D1}$—OOC—$R_A$—COOH + (y)HO—$R_{D2}$]OH⟶(n-1)$H_2$O+ (y/n)HOOC—$R_A$—COO—$R_{D1}$—OOC—$R_{D2}$—OOC—$R_A$''' " should be -- (y)HOOC—$R_A$—COO—$R_{D1}$—OOC—$R_A$—COOH + (y)HO—$R_{D2}$—OH⟶(n-1)$H_2$O + (y/n) HOOC [$R_A$—COO—$R_{D1}$—OOC—$R_{D2}$]OOC—$R_A$''' --.

Col. 13, beginning on line 21, "HOOC—$R_H$]—OH + HOOC—$R_{H2}$—OH $H_2$O + HOOC— $R_{H1}$—OOC—$R_{H2}$—OOC—$R_{H2}$OOC—$R_{H1}$]$_n$OH" should be --HOOC—$R_{H1}$—OH + HOOC—$R_{H2}$—OH $H_2$O + HOOC—[$R_{H1}$—OOC—$R_{H2}$—OOC—$R_{H2}$—OOC—$R_{H1}$]$_n$ OH --.

Col. 13, line 39, "Composite" should be --Composites--.

Col. 13, line 45, "polyesters" should be --polyester--.

UNITED STATES PATENT AND TRADEMARK OFFICE
CERTIFICATE OF CORRECTION

PATENT NO. : 4,481,353
DATED : November 6, 1984
INVENTOR(S) : Nyilas et al.

It is certified that error appears in the above–identified patent and that said Letters Patent are hereby corrected as shown below:

Col. 15, beginning on line 1, "$- R_A-COO-R_H-COO-R_D-OOC-R_H-OOC]$" should be $-- [R_A-COO-R_H-COO-R_D-OOC-R_H-OOC] --$.

Col. 15, beginning on line 47, "$-OOC-R_{A1}-COO-R_D-OOC-R_{A2}-COO-R_D]$" should be $--[OOC-R_{A1}-COO-R_D-R_{A2}-COO-R_D] --$.

Col. 16, line 20, "$-R_A-COO-R_{D1}-OOC-R_{D2}]$" should be $--[R_A-COO-R_{D1}-OOC-R_{D2}] --$.

Signed and Sealed this

Eighth Day of October 1985

[SEAL]

Attest:

DONALD J. QUIGG

Attesting Officer

Commissioner of Patents and
Trademarks—Designate